US011338076B2

(12) United States Patent
Kusters et al.

(10) Patent No.: US 11,338,076 B2
(45) Date of Patent: May 24, 2022

(54) SYSTEM AND METHOD OF USING FREQUENCY ANALYSIS TO MONITOR FLOW RATES

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 788 days.

(21) Appl. No.: 16/124,796

(22) Filed: Sep. 7, 2018

(65) Prior Publication Data

US 2019/0070354 A1    Mar. 7, 2019

Related U.S. Application Data

(60) Provisional application No. 62/555,196, filed on Sep. 7, 2017.

(51) Int. Cl.
*A61M 1/36* (2006.01)
*A61M 1/16* (2006.01)
(Continued)

(52) U.S. Cl.
CPC ........ *A61M 1/3693* (2013.01); *A61M 1/1647* (2014.02); *A61M 1/3496* (2013.01);
(Continued)

(58) Field of Classification Search
CPC .............. A61M 1/1647; A61M 1/3496; A61M 1/3621; A61M 1/3693; A61M 1/3663; A61M 1/367; B04B 11/02; B04B 13/00
See application file for complete search history.

(56) References Cited

U.S. PATENT DOCUMENTS 5,868,696 A   2/1999  Giesler et al.
6,582,349 B1  6/2003  Cantu et al.
(Continued)

FOREIGN PATENT DOCUMENTS

WO    2014039086 A1   3/2014

OTHER PUBLICATIONS

Cerna et al. "The Fundamentals of FFT-Based signal analysis and Measurement", Jul. 2000 (Year: 2000).*

*Primary Examiner* — Benjamin J Klein
(74) *Attorney, Agent, or Firm* — Cook Alex Ltd.

(57) ABSTRACT

A system for controlling a fluid procedure comprising a reusable separation apparatus controlled by a microprocessing controller. A sterile circuit is configured to associate with the reusable separation apparatus and provide a first fluid flow path in association with a pressure sensor in communication with the controller and a first pump configured to transmit pulsatile pressure signals to the pressure sensor during operation in association with the first fluid flow path. The reusable apparatus and the controller are configured to receive from the pressure sensor pressure signals comprising the pulsatile pressure signals, perform a frequency analysis of the pressure signals received by the pressure sensor over a time duration, derive a first rotation rate of the first pump or a first fluid flow rate at the first pump from the frequency analysis, and provide a response action based on the first rotation rate or the first fluid flow rate.

26 Claims, 11 Drawing Sheets

(51) Int. Cl.
*A61M 1/34* (2006.01)
*B04B 13/00* (2006.01)
*B04B 11/02* (2006.01)

(52) U.S. Cl.
CPC .......... *A61M 1/367* (2013.01); *A61M 1/3621* (2013.01); *A61M 1/3639* (2013.01); *A61M 1/3663* (2013.01); *B04B 11/02* (2013.01); *B04B 13/00* (2013.01)

(56) References Cited

U.S. PATENT DOCUMENTS

2011/0112595 A1* 5/2011 Solem .................... G01N 33/49
 607/17
2015/0174307 A1* 6/2015 Eckman .................. A61B 5/72
 600/17

\* cited by examiner

SYSTEM AND METHOD OF USING FREQUENCY ANALYSIS TO MONITOR FLOW RATES

CROSS-REFERENCE TO RELATED APPLICATIONS

This application claims the benefit of U.S. Provisional Patent App. No. 62/555,196 filed Sep. 7, 2017, which is expressly incorporated herein by reference in its entirety.

FIELD OF THE DISCLOSURE

The present disclosure relates generally to systems and methods for processing biological fluid and, in particular to systems and methods for using frequency analysis to monitor flow rates during a biological fluid procedure.

BACKGROUND

A variety of available blood processing systems allows for the collection and processing of particular blood components, rather than whole blood, from donors or patients. In the case of a blood donor, whole blood is drawn from the donor, a desired blood constituent isolated and collected, and the remaining blood components returned to the donor. By removing only particular constituents rather than whole blood, it takes the donor's body a shorter time period to recover to normal blood levels, thereby increasing the frequency with which the donor may donate blood. It is beneficial to increase in this manner the overall supply of blood constituents made available for health care, such as red blood cells (RBCs), leukocytes, plasma, and/or platelets, etc.

The separation phase of blood components from whole blood may be achieved through a spinning membrane or centrifugation, in which whole blood is passed through a centrifuge or membrane after it is withdrawn from the patient. To avoid contamination and possible infection of the patient, the blood is preferably contained within a sealed, sterile fluid flow system during the entire separation process. Typical blood processing systems thus may include a permanent, reusable hardware assembly containing the hardware (drive system, pumps, valve actuators, programmable controller, and the like) that pumps the blood, and a disposable, sealed and sterile fluid circuit that is mounted in cooperation on the hardware. In the case of separation via centrifugation, the hardware assembly includes a centrifuge that may engage and spin a separation chamber of the disposable fluid circuit during a blood separation step. The blood, however, may make actual contact only with the fluid circuit, which assembly may be used only once and then discarded. In the case of separation via a spinning membrane, a disposable single-use spinning membrane may be used in cooperation with the hardware assembly and disposable fluid circuit.

In the case of separation via centrifugation, as the whole blood is spun by the centrifuge, the heavier (greater specific gravity) components, such as red blood cells, move radially outwardly away from the center of rotation toward the outer or "high-G" wall of the separation chamber of the fluid circuit. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid circuit.

In the case of separation via a spinning membrane, whole blood may be spun within a disposable spinning membrane, rather than within a separation chamber of a fluid circuit. Larger molecules, such as red blood cells, may be retained within one side of the membrane, while the smaller molecules, such as plasma, may escape through the pores of the membrane to the other side of the membrane. Various ones of these components can be selectively removed from the whole blood by forming appropriately located outlet ports in the housing of the membrane column. Various types of columns with different pore sizes may be used, depending on the components to be separated.

It is common for two or more medical solutions and/or fluids to be flowing simultaneously during blood processing procedures. Flow of various fluids may be controlled and directed by pumps, e.g., peristaltic pumps. For example, saline solution, anti-coagulant solution, additive solutions, replacement fluids, RBCs, WBCs, platelets, plasma, etc. may be in flow throughout a blood processing procedure along fluid pathways, some of which may be disposed along one or more pumps. Regulating and monitoring flow and pump rates through the various fluid pathways may be desirable for conducting consistent and successful blood processing procedures.

SUMMARY

According to an exemplary embodiment, the present disclosure is directed to a system for monitoring and controlling a fluid procedure. The system comprises a reusable separation apparatus controlled by a microprocessing controller. The reusable separation apparatus comprises a pressure sensor in communication with the controller. The system also comprises a sterile circuit configured to associate with the reusable separation apparatus and provide a first fluid flow path in association with the pressure sensor and a first pump configured to transmit pulsatile pressure signals to the pressure sensor during operation in association with the first fluid flow path. The reusable apparatus and the controller are configured to receive from the pressure sensor one or more pressure signals comprising the pulsatile pressure signals transmitted by the first pump, perform a frequency analysis of the one or more pressure signals received by the pressure sensor over a time duration, derive a first rotation rate of the first pump or a first fluid flow rate at the first pump from the frequency analysis, and provide at least one response action based on the first rotation rate or the first fluid flow rate.

According to an exemplary embodiment, the present disclosure is directed to a computer-implemented method for monitoring fluid flow rates during a fluid procedure. The method comprises providing a first pump configured to transmit pulsatile signals during operation in association with a first fluid flow path, providing a sensor in communication with the first fluid flow path and configured to receive the pulsatile signals from the first pump, providing a controller in communication with the sensor and the first pump, performing via the controller a frequency analysis on one or more signals received by the sensor over a time duration, calculating a first rotation rate of the first pump or a first fluid flow rate at the first pump from the frequency analysis, and providing at least one response action based on the first rotation rate or the first fluid flow rate.

According to an exemplary embodiment, the present disclosure is directed to a system for monitoring and controlling a fluid procedure. The system comprises a reusable separation apparatus controlled by a microprocessing controller and a pressure sensor in communication with the controller. The system also comprises a sterile circuit configured to associate with the reusable separation apparatus and configured to provide a first fluid flow path in association with a first pump and the pressure sensor and a second fluid flow path in association with a second pump. The first pump is configured to transmit pulsatile pressure signals to the pressure sensor during operation in association with the first fluid flow path and the second pump is also configured to transmit pulsatile pressure signals to the pressure sensor during operation in association with the second fluid flow path. A resilient element is in communication with the first and second fluid flow paths. The resilient element comprises a material reactive to pressure changes originating from one or both of the first and second fluid flow paths. The reusable apparatus and the controller are configured to receive from the pressure sensor one or more pressure signals comprising pulsatile pressure signals from the first and second pumps, perform a fast Fourier transform of the one or more pressure signals received by the pressure sensor over a time duration, derive a first rotation rate of the first pump or a first fluid flow rate at the first pump from the frequency analysis, derive a second rotation rate of the second pump or a second fluid flow rate at the second pump from the frequency analysis, and provide at least one response action based on a) the first rotation rate or the first fluid flow rate and b) the second rotation rate or the second fluid flow rate.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may allow pump flow measurements to be made without the use of scales or tachometers.

Some embodiments may allow pump flow measurements to be made without a sensing mechanism dedicated to each pump.

Some embodiments may allow for calculating and monitoring flow rates at multiple pumps with a single sensor.

Some embodiments may reduce the cost of blood processing systems by eliminating sensing hardware.

There have been continuing efforts to automate the apparatus and systems used in the collection and/or processing of blood and blood components, and an automated blood component separator for such collection/processing may be employed. One class of such automated separators employs relatively rotating surfaces, at least one of which carries a porous membrane. An example of such a membrane separator is disclosed in PCT Patent Application Publication No. WO 2014/039086 A1, which is incorporated by reference in its entirety, although any suitable membrane separator may be used. Another class employs a centrifuge that utilizes centrifugal separation principles. An exemplary centrifugal separator is disclosed in U.S. Pat. Nos. 5,868,696 and 6,582,349, which are incorporated by reference in their entireties, although any suitable centrifugal separator may be used.

Both membrane separation and centrifugal separation systems may involve a durable processing system or device used in combination with a disposable processing set or circuit. The durable processing system may include a pump assembly that interacts with one or more of the components of the disposable circuit to draw blood or other bodily fluid from a blood source and move the blood or bodily fluid to another location within the disposable circuit by moving fluid through a fluid flow path. In one embodiment, the pump assembly may incorporate peristaltic pumps, which are disclosed in the aforementioned U.S. Pat. No. 5,868,696.

Figure 1:
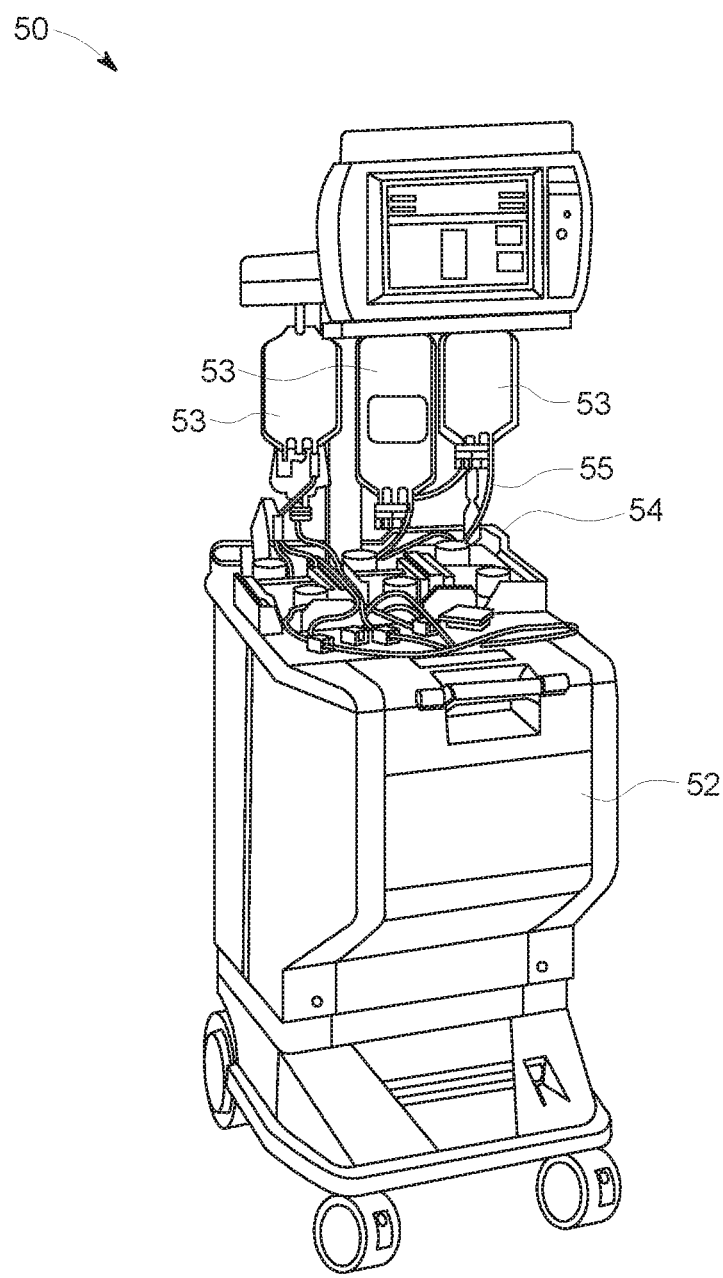
FIG. 1 is a perspective view of an automated medical fluid processing device that may be used in the collection and other processing steps of biological fluids, according to an exemplary embodiment.
Figure 2:
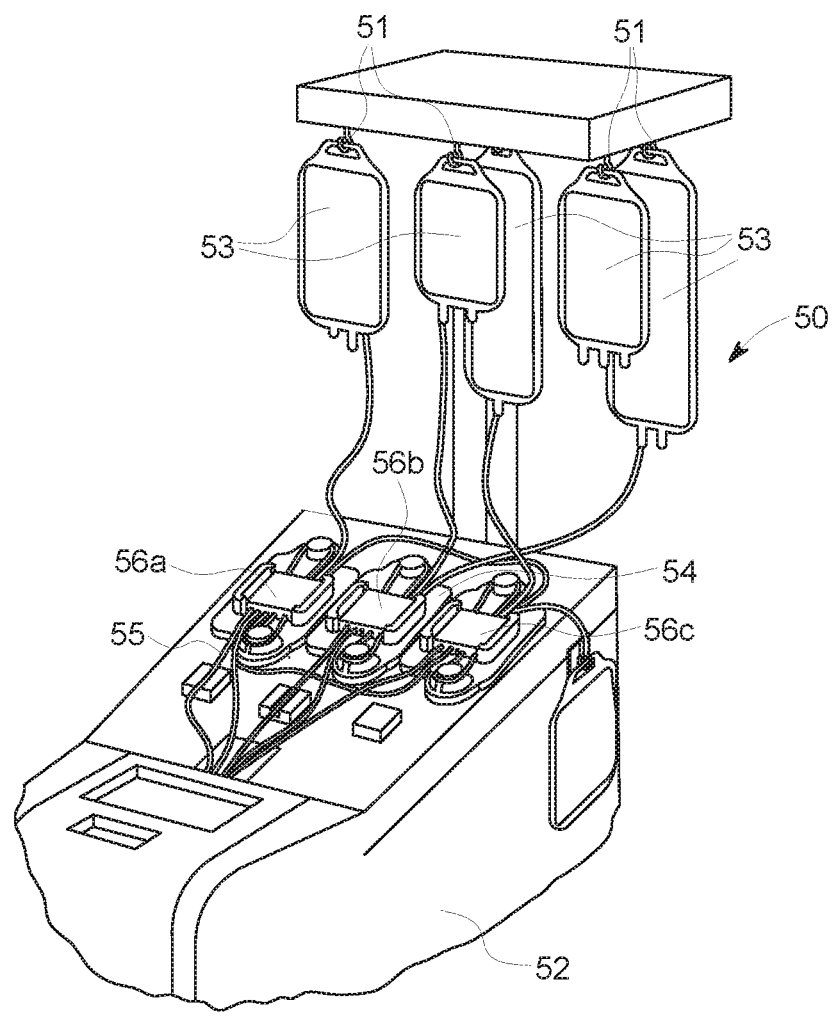
FIG. 2 is an enlarged perspective view of the front panel of the device of FIG. 1 with a disposable processing set mounted on the device, according to an exemplary embodiment.

FIGS. 1 and 2 show an exemplary separation device useful in the separation and processing of blood components, e.g., red blood cells, white blood cells, platelets, plasma, etc. The separator 50 may include a hardware component 52 and a disposable processing kit 54 mounted thereon. In one embodiment, the separation principle used by the separator may be based on membrane separation, but an automated separator based on a different separation principle (e.g., centrifugation) may also be used.

With respect to the device shown in FIGS. 1 and 2, the hardware component 52 may comprise a plurality of hangers 51 for hanging fluid containers 53. One or more hangers 51 may also function as a weight scale that is in communication with a pre-programmed controller of the hardware component 52. Disposable kit 54 may include plastic containers 53 for holding fluid, and tubing 55 defining flow paths for movement of the blood, blood components and other medical fluids through the fluid circuit of kit 54.

Figure 3:
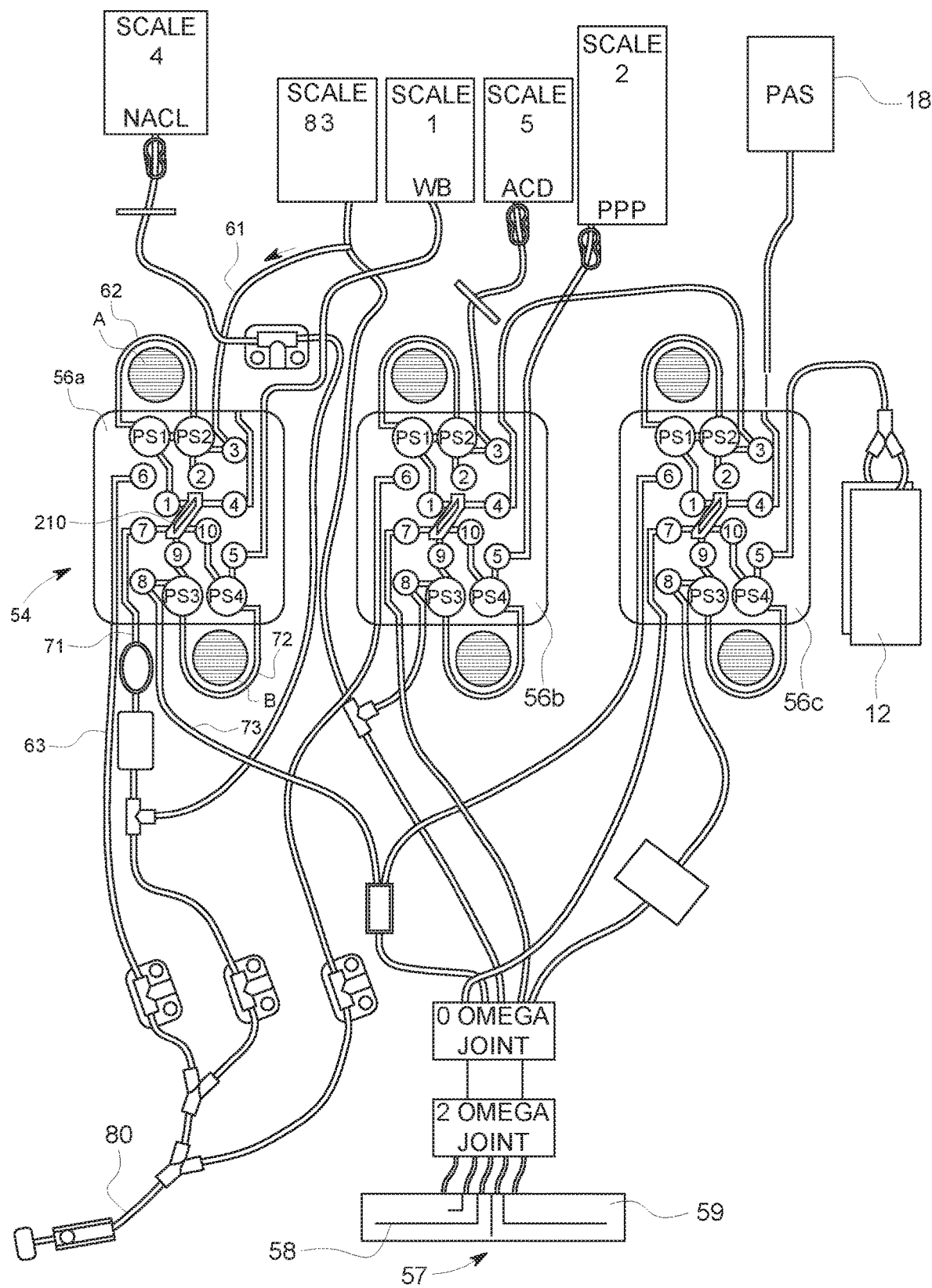
FIG. 3 is a diagram showing the disposable processing set of FIG. 2, according to an exemplary embodiment.

The disposable processing kit 54 may also include one or more cassettes 56 (i.e., cassettes 56a, 56b and 56c shown in FIG. 2) which may interface with the front panel of hardware component 52. Cassettes 56a, 56b and 56c may include flow paths, pressure sensors, and valve stations. A series of pneumatically or electrically operated valves (numbered 1-10 in FIG. 3, for example) under the control of the pre-programmed controller of hardware component 52 may selectively allow and restrict liquid flow through the flow paths of the cassette and ultimately through the tubing of disposable kit 54. One or more pressure sensors disposed on the front panel of hardware component 52 may also be in communication with the controller to monitor the fluid procedure. Possible locations for pressure sensors are numbered PS1-4 in FIG. 3, although the pressure sensors may be disposed at any suitable location. Disposable kit 54 may further include a processing chamber shown generally at 57 of FIG. 3 (which may be mounted on a rotor/spool of a centrifuge). Processing chamber 57 may have a sub-chamber 58 wherein blood or blood components are separated under the influence of centrifugal force (i.e., the "separation chamber") and a sub-chamber 59 where blood components from sub-chamber 58 may be further processed, separated and/or collected (i.e., the "concentration chamber"). In a spinning membrane separation system, the separation chamber and concentration chamber may comprise a spinning membrane separator.

Figure 4:
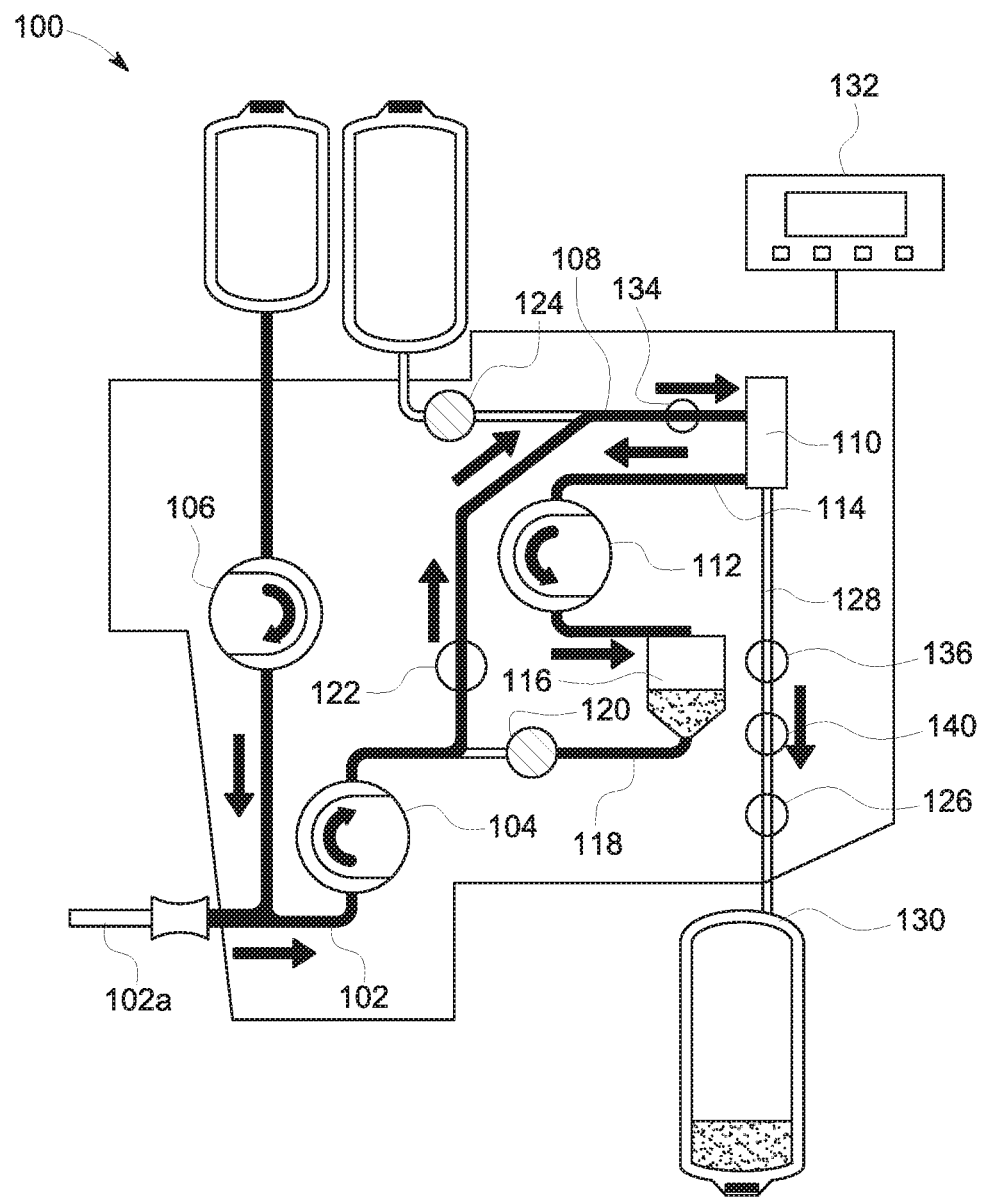
FIG. 4 is a schematic representation of a membrane filtration system, according to an exemplary embodiment.

FIG. 4 is a schematic view of one embodiment of a spinning membrane separation system 100, which will be used to demonstrate certain embodiments. Arrows in FIG. 4 show fluid flow direction during a draw cycle of a biological fluid processing procedure. The system 100 may include a source line 102 that may be configured to connect via an access device 102a to a fluid source, which may be a patient/donor or a source fluid container (not illustrated). Source line 102 may be acted on by a pump 104. In an embodiment in which source fluid is whole blood, anticoagulant may be added to the whole blood in the source line 102 by way of a second pump 106. The source line 102 may connect to a processing line 108 for introducing, e.g., anticoagulated whole blood, into the inlet of a spinning membrane separator 110. A third pump 112 may act on a first outlet line 114 to flow separated retentate (e.g., cellular material in a blood component procedure) to a container 116. In one embodiment, the contents of container 116 may be stored and/or further processed. In another embodiment, container 116 may be connected by way of return line 118 to the source line 102 for the return of the separated cellular material to, e.g., the donor. A filtrate line 128 may be connected to a second outlet of the separator 110 for flowing separated filtrate (e.g., plasma in a blood component procedure) to a filtrate collection container 130 for storage and/or further processing. Although not depicted in FIG. 4, in one embodiment, the filtrate container 130 may be connected to the source line 102 if an objective of the procedure is to, e.g., return the filtrate to the donor and instead collect the retentate.

Flow through the several lines may be selectively controlled by operation of clamps 120, 122, 124 and 126. The operation of the pumps 104, 106, 112, the clamps 120, 122, 124, 126, and the speed of rotation of the spinning membrane may be automatically controlled by a programmable controller 132. Pumps 104, 106, 112 may be associated with one or more tachometer for providing pump rate information to the controller 132. The controller 132 may be preprogrammed to operate the system 100 in accordance with a number of different separation protocols and may include a user interface to permit an operator to input information into and/or receive information from the controller. According to various embodiments, controller 132 may be integral to system 100 or remotely located with respect to system 100 (e.g., connected via cable and/or network).

Figure 5:
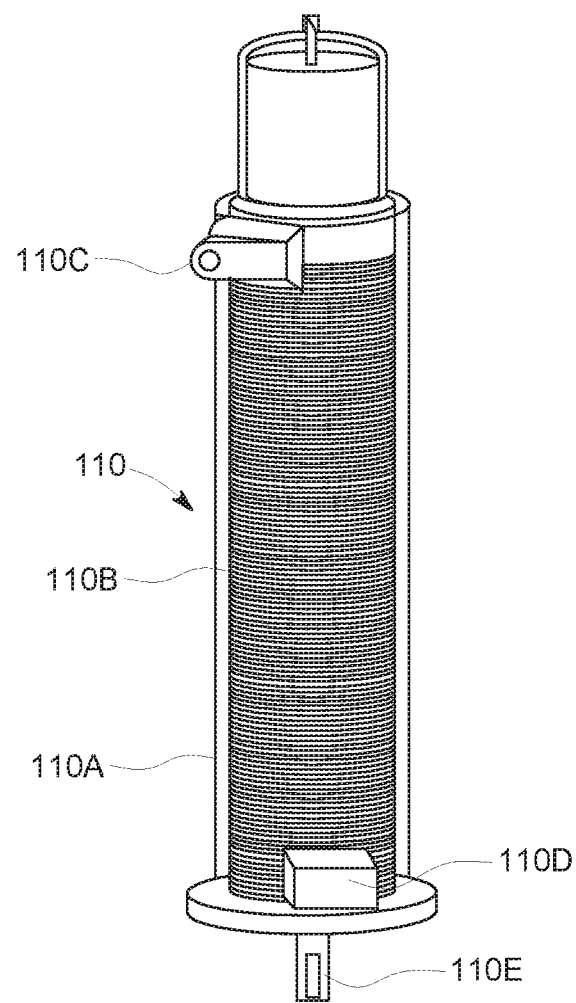
FIG. 5 is a schematic representation of a spinning membrane separator suitable for use in the system of FIG. 4, with portions shown in ghost line to show interior detail, according to an exemplary embodiment.

With reference to FIG. 5, the spinning membrane separator 110 may comprise a housing 110a, with a rotary spinner 110b mounted for relative rotation within the housing 110a and have a filter membrane on the surface thereof. The housing 110a may further include an inlet 110c in fluid communication with the processing line 108 of FIG. 4, a first outlet 110d in fluid communication with the retentate line 114, and a second outlet 110e in fluid communication with the filtrate line 128. A pressure sensor 134 may be associated with the processing line 108, adjacent the inlet 110c, for providing signals to the controller 132 by which transmembrane pressure may be determined. An optical sensor 140 may be positioned along one or more lines 102, 108, 114, 128 and also provide signals to the controller 132 by which fluid properties within the lines may be determined. An example of a spinning membrane separator is disclosed in the aforementioned PCT Patent Application Publication No. WO 2014/039086 A1.

During the biological fluid procedure, the controller 132 may be programmed to process input from various sensors, e.g., weight scales, tachometers, optical sensors, pressure sensors, etc., to control and monitor the separation process. Based on the input from various sensors and a control process/algorithm, the controller may be configured to provide response actions, such as altering fluid flow rates, altering pump rates, altering separation rates, altering spin rates, altering target parameters, suspending the procedure, and/or alerting an operator. For example, in an embodiment in which source fluid is connected to the source line 102 (FIG. 4) via a container hung on a sensor in the form of a weight scale (not illustrated) in communication with the controller, the controller may calculate flow rate at the processing line 108 into the separator 110 by using the change in weight information at the weight scale to derive change in volume (V) over time (t), which may be used to calculate flow rate (flow rate=$\Delta V/\Delta t$). In another example, in an embodiment in which the inlet pump 104 having a known stroke volume (i.e., volume of fluid moved with each rotation) is associated with a sensor in the form of a tachometer in communication with the controller, the controller may calculate flow rate at the processing line 108 into the separator 110 by using tachometer readings to calculate flow rate (flow rate=pump rotation rate×stroke volume).

Determination of the flow rates of fluid being moved by one or more pumps may be desirable for a successful fluid procedure. For example, in a membrane separation system such as the one depicted in FIGS. 4 and 5, comprising a pump 104 actuating flow into the separator 110 and a pump 112 actuating flow out of the separator at one of the two exit lines 114, 128, the flow rate ($Q_{filtrate}$) of fluid exiting the outlet 110e not associated with a pump is the difference between the flow rate ($Q_{inlet}$) of source fluid entering the inlet 110c, effected by pump 104, and the flow rate ($Q_{retentate}$) of fluid exiting the outlet 110d, effected by pump 112. The pump rates for pumps 104 and 112 may therefore directly affect filtration flow rate and separation efficiency. Equation 1 describes the relationship among the three flow rates:

$$Q_{filtrate} = Q_{inlet} - Q_{retentate} \quad \{\text{Equation 1}\}$$

Calculating and monitoring flow rates at multiple pumps with a single sensor in the form of a pressure sensor may be achieved by measuring pressure at a location at which combined pressures exerted by the multiple pumps may be detected. For example, referring to FIG. 4, the pressure sensor 134 may be disposed adjacent the inlet 110c, where pressure signals contributed by both pumps 104 and 112 may be received. The pressure sensor 134 may be used both for determining transmembrane pressure and separation efficiency at the membrane and also for determining individual pump rates, as will be demonstrated below.

Figure 6:
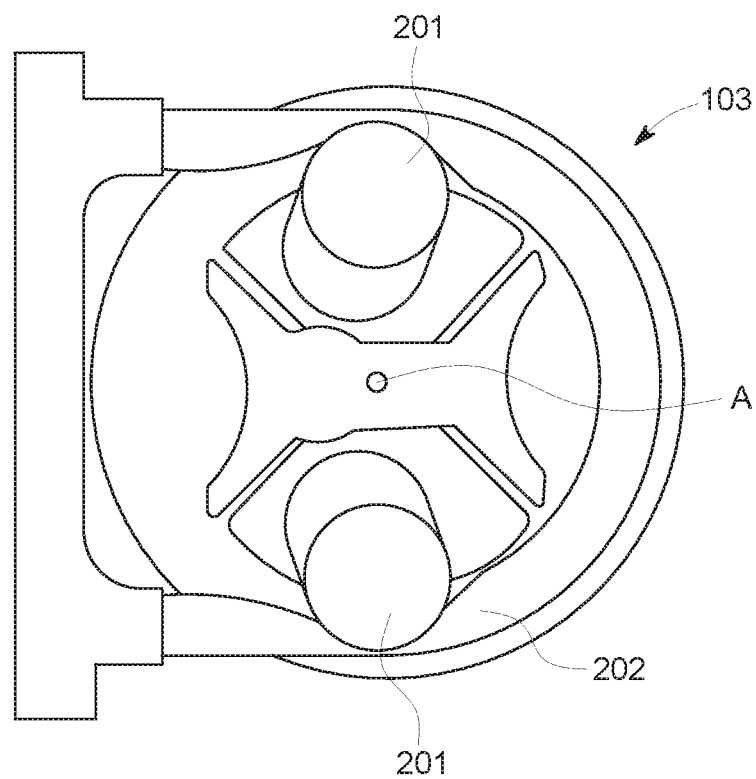
FIG. 6 is a schematic view of a peristaltic pump, according to an exemplary embodiment.
Figure 7:
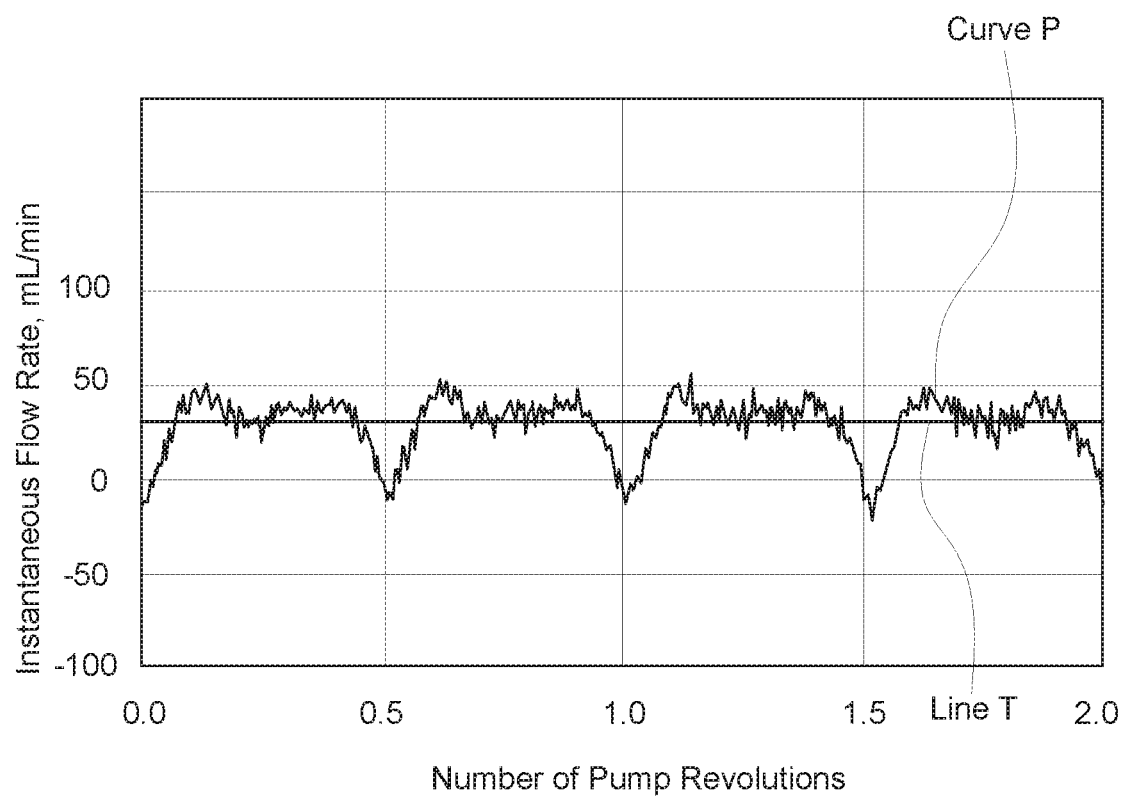
FIG. 7 is a graph of flow rate at a pump plotted over the number of pump revolutions, according to an exemplary embodiment.

FIG. 6 is a schematic view of a peristaltic pump 103, such as one that may be used for pumps 104, 106, and/or 112 depicted in FIG. 4. Pump 103 may have two rollers 201 configured to push fluid along tubing 202 about an axis A, according to an exemplary embodiment. FIG. 7 is a graph of flow rate (in mL/min) at a pump plotted over the number of pump revolutions, generated by a pump having two rollers, such as pump 103 of FIG. 6. Curve P represents actual flow rate along the fluid flow path, e.g., tubing 202 of FIG. 6, measured by an ultrasonic flow meter set to 100 Hz when the pump has been configured to pump at a targeted rate of 30 mL/min (Line T). Curve P shows that flow signal data generated by the peristaltic pump and measured by the flow meter is pulsatile in nature. Each half-revolution along Curve P (No. of pump revolution=0.5, 1.0, 1.5, etc.) is associated with a temporary decrease in the flow rate due to a roller engaging with the flow path. Because the pump that generated Curve P comprises two rollers, a roller re-engages with the flow path every one-half rotation.

In an embodiment in which multiple pulsatile signal transmitters, e.g., peristaltic pumps, provide signals to a sensor, the sensor may receive cumulative signals from both pulsatile signal transmitters. For example, referring to FIG. 4, inlet pump 104 may provide a first pulsatile signal, and retentate pump 112 may provide a second pulsatile signal. Given that the filtrate flow rate may be described according to Equation 1 based on the inlet pump rate and the retentate pump rate, the filtrate flow may exhibit flow rate pulse frequencies of both pumps 104 and 112.

The filtrate flow rate $Q_{filtrate}$ may also be expressed in relation to a resilient element disposed between the pulsatile signal transmitters. In the embodiment of FIG. 4, the resilient element comprises the membrane within the separator 110. Flow of fluid through a porous medium is described by Darcy's Law in the following equation:

$$Q_{filtrate} = \frac{K * A * \Delta P}{\mu * L} \quad \{\text{Equation 2}\}$$

In Equation 2, $Q_{filtrate}$=filtrate flow rate through the membrane, K=membrane permeability, A=membrane surface area, $\Delta P$=transmembrane pressure, L=membrane thickness, and $\mu$=fluid viscosity. Given that K, A, L, and $\mu$ generally remain constant, Equation 2 indicates that $Q_{filtrate}$ is proportional to transmembrane pressure $\Delta P$. Given that the filtrate flow rate, which exhibits flow rate pulse frequencies of both pumps 104 and 112, is a function of transmembrane pressure according to Equation 2, the transmembrane pressure also reflects the flow rate pulse frequencies of both pumps 104 and 112. The transmembrane pressure signals received by pressure sensor 134 of FIG. 4 disposed adjacent the inlet 110c may also comprise the flow rate pulse frequencies of pumps 104 and 112.

The frequency at which a pump rotates may be expressed as a function of flow rate according to the following equation:

$$Freq_{rot} = \frac{Q}{\text{Stroke volume}} \times \frac{1 \text{ min}}{60 \text{ sec}} \times \text{No. of pump rollers} \quad \{\text{Equation 3}\}$$

Given that stroke volume and the number of pump rollers of a pump generally remain constant, Equation 3 indicates that a pump's frequency of rotation may be expressed as a function of flow rate.

Figure 8A:
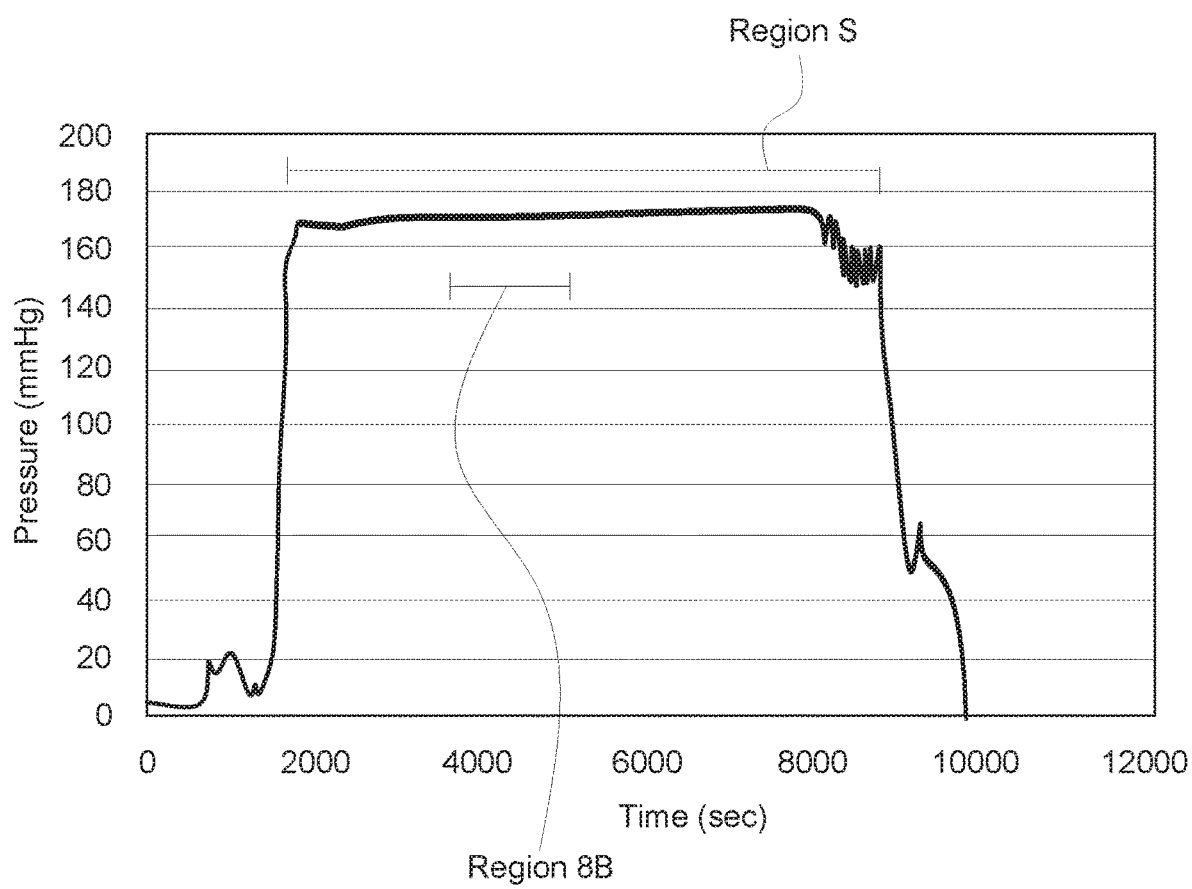
FIG. 8A is a representative graph of pressure signals measured over time at pressure sensor during a membrane separation procedure, according to an exemplary embodiment.
Figure 8B:
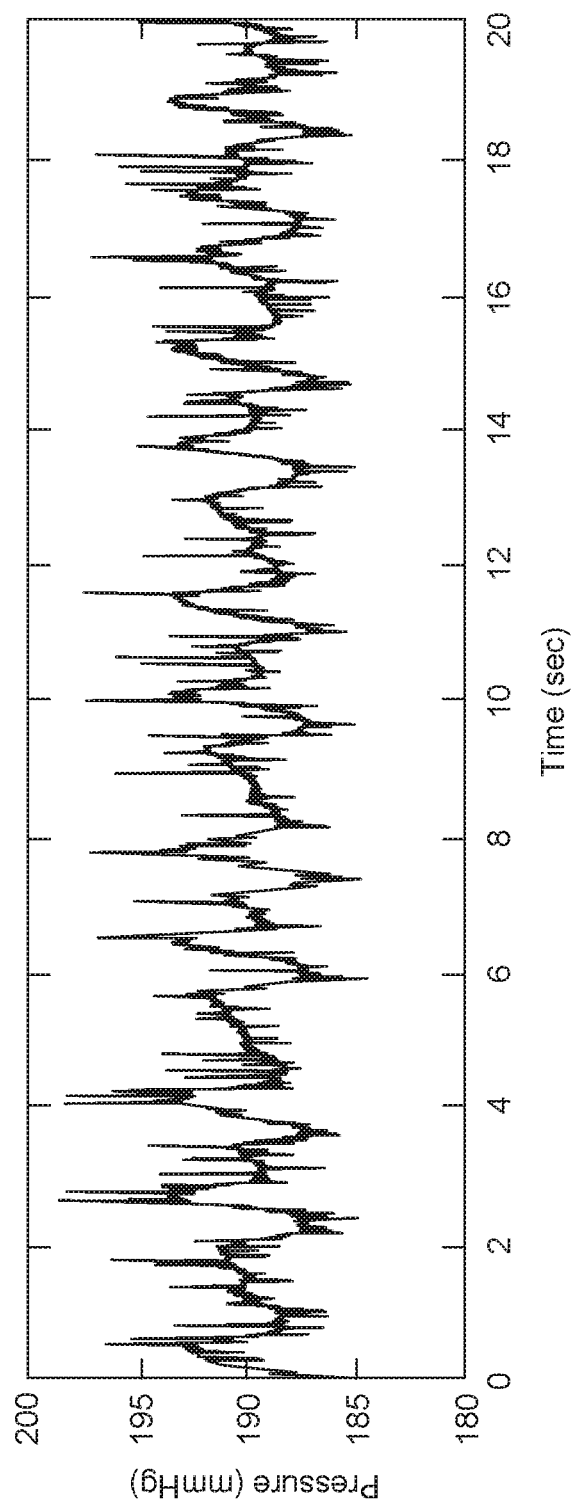
FIG. 8B is an expanded view of a region of the graph of FIG. 8A during a specific time period, according to an exemplary embodiment.

FIG. 8A is a representative graph of pressure signals measured over time at pressure sensor 134 during a membrane separation procedure performed by the system 100 of FIG. 4. The pressure sensor 134 is in communication with multiple pulsatile signal transmitters 104, 112. The controller has been configured to pump source fluid at pump 104 at 40 mL/min and pump retentate fluid at pump 112 at 23.4 mL/min. Region S of FIG. 8A where pressure is approximately 160-180 mm Hg indicates a time period in which active separation is taking place. FIG. 8B is an expanded view of Region 8B of the pressure graph of FIG. 8A during a 20-second period while active separation is taking place.

Figure 9:
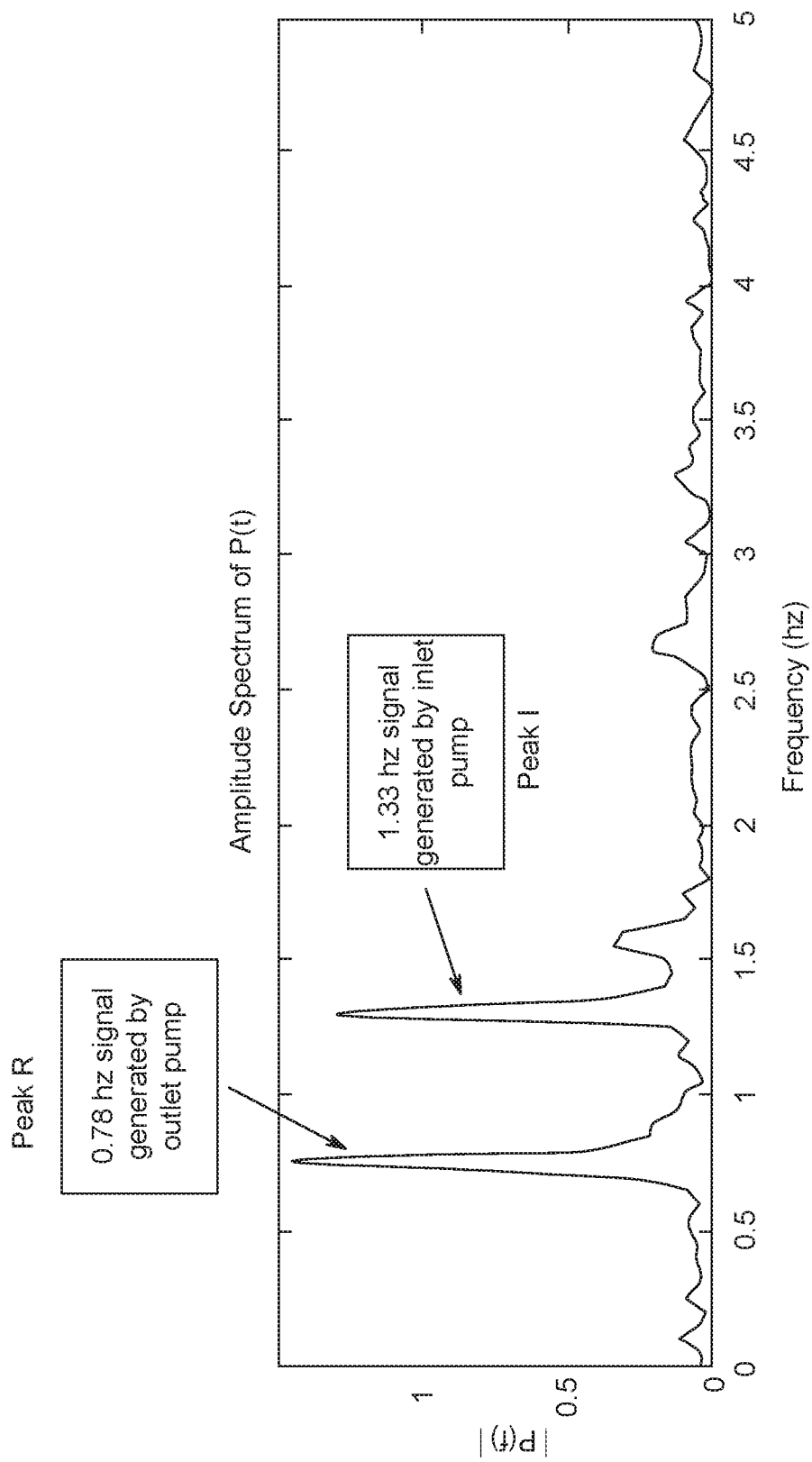
FIG. 9 is a single side frequency amplitude spectrum derived from a frequency analysis of FIG. 8B, according to an exemplary embodiment.

A frequency analysis may be conducted on the raw pressure data of FIG. 8B to obtain a relationship between pressure and frequency. In one embodiment, the frequency analysis may comprise computing a discrete Fourier transform (DFT) via a standard fast Fourier transform (FFT) algorithm to convert the pressure data of FIG. 8B from a time domain to a frequency domain. FIG. 9 shows a resulting single side frequency amplitude spectrum derived from the FFT conversion of FIG. 8B. FIG. 9 shows that a first peak (Peak R) occurs at 0.78 Hz, and a second peak (Peak I) occurs at 1.33 Hz. The two peaks R and I correspond to respective pump rotation rates of the retentate pump 112 and the inlet pump 104. Between the two frequencies 0.78 and 1.33 Hz, the higher frequency of 1.33 Hz may be deduced to correspond to the inlet pump 104 because fluid is known to flow into the separator 110 faster than it flows out.

Equation 3 above may be rearranged to solve for flow rates produced by each frequency detected by the pressure sensor. Pumps 104 and 112 have known stroke volumes of 1.0 mL/rotation, and the following flow rates may be calculated from FIG. 9:

$$Q_{inlet} = \frac{1.33 \text{ Hz} * 1.0 (\text{mL/rotation}) * 60}{2} = 40 \text{ mL/min}$$

$$Q_{retentate} = \frac{0.78 \text{ Hz} * 1.0 (\text{mL/rotation}) * 60}{2} = 23.4 \text{ mL/min}$$

Comparing with commanded flow rates of 40 mL/min for the inlet pump flow rate and 23.4 mL/min for the retentate pump flow rate programmed into the controller and verified as actual flow rates by a flow meter, pressure data analysis at a pressure sensor in communication with multiple pulsatile flow and a resilient element has shown to accurately determine individual flow rates.

In one embodiment, throughout a fluid procedure, the controller may be programmed to continuously, periodically, and/or on a rolling basis process pulsatile signal input from a pressure sensor to determine flow rates used for controlling the separation process. For example, flow rates at each pump may be calculated by analyzing pressure signals over a specific duration, e.g., 2-10 seconds, on a rolling basis, depending on pump rotation frequency. At lower pump rotation frequencies (e.g., 3 seconds per rotation), it may be desirable to increase the duration over which the signal is processed in order to capture at least one or more rotations. For example, for a pump taking 3 seconds per rotation, 9 seconds of signal processing would capture 3 periods of the pump's signal. At higher pump rotation frequencies (e.g., 0.5 seconds per rotation), the duration over which the signal is processed may be shorter than at lower pump rotation frequencies. For example, for a pump taking 0.5 seconds per rotation, only 1.5 seconds of signal processing would capture 3 periods of the pump's signal. In one embodiment, the controller may be configured to analyze pressure signals for a duration capturing at least one period. In another embodiment, the controller may be configured to analyze pressure signals for a duration capturing at least three periods.

While a frequency analysis to determine individual flow rates has been described in the context of a membrane separation system, flow rates may be determined via frequency analysis in other systems comprising any resilient element disposed between two or more pulsatile signal transmitters, wherein the resilient element is capable of transferring at least a portion of total pressure between two flow paths in which the signal transmitters are disposed while also providing resistance to pressure transfer between the two flow paths. For example, referring to FIG. 3, flow rates at pump A and pump B of cassette 56*a* may be determined by analyzing signal data at one of the pressure sensors PS1-PS4 where combined pressures exerted by the pumps A and B may be detected. In one embodiment, one or more of valves 1-10 of cassette 56*a* may function as a resilient element impermeable to some molecules, e.g., liquid, when the valve is closed but capable of transferring pressure from one valve to another, to allow for frequency analysis. In another embodiment, a membrane 210 may be disposed between a fluid flow path in association with pump A and a fluid flow path in association with pump B, wherein the membrane 210 is configured to transfer at least a portion of total pressure between the two flow paths. The membrane 210 may or may not be permeable to liquid flow.

In one embodiment, a pressure sensor may be disposed at location PS4 within cassette 56*a*. The flow path associated with pump A may comprise a path from container 83 into tubing 61 leading to open valve 3. By shutting valve 2, the flow may be directed to tubing 62 and pumped by pump A past open valve 6 into tubing 63. The flow path associated with pump B may comprise a path from tubing 71 leading to open valve 7. By shutting valves 1, 2, 4, 5 and 9, the flow may be directed to open valve 10 and pumped into tubing 72 past open valve 8 from which the fluid may exit cassette 56*a* into tubing 73.

Figure 10:
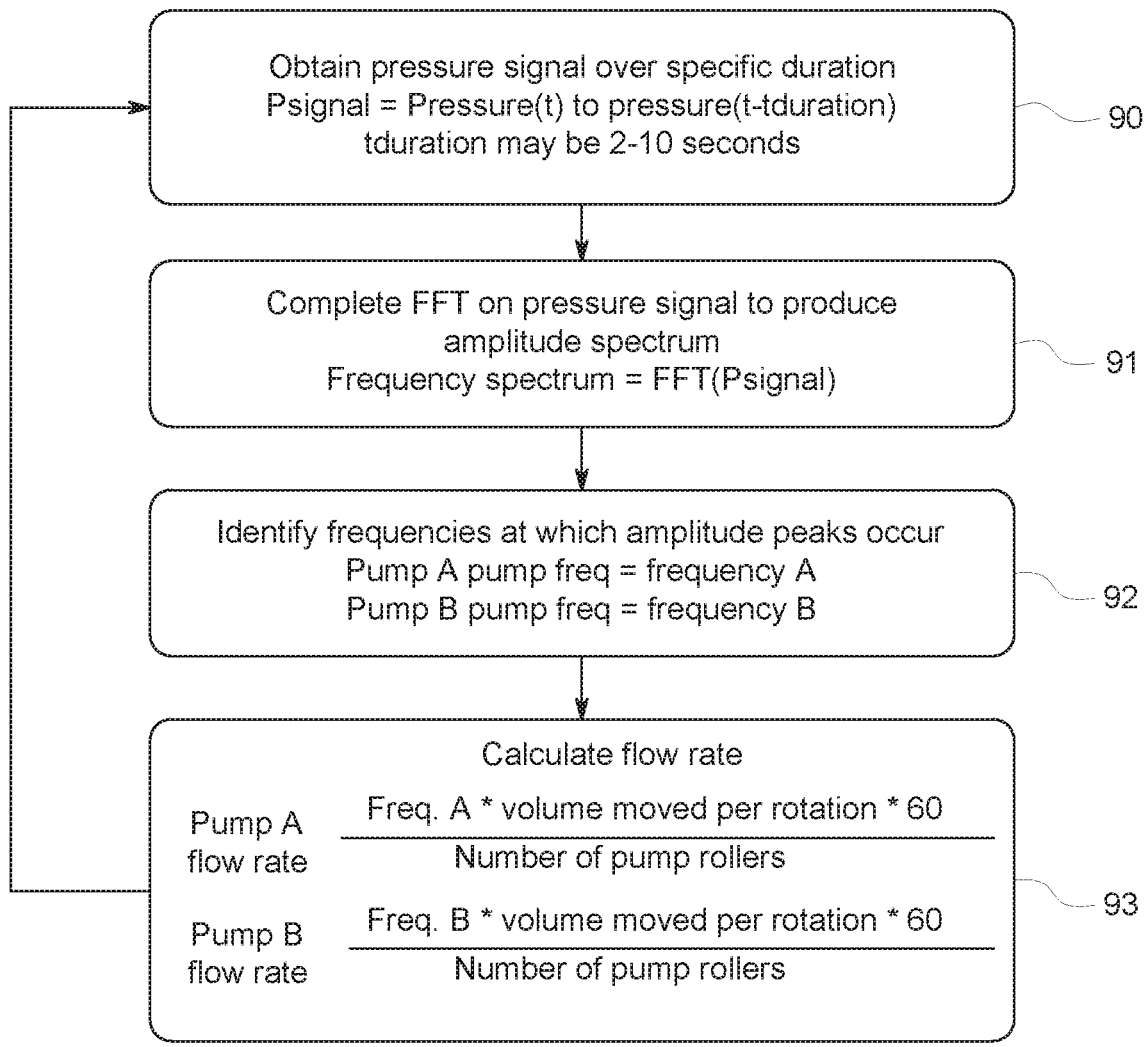
FIG. 10 is a flow diagram illustrating the steps for determining individual fluid flow rates from a sensor receiving cumulative signals from multiple pulsatile signal transmitters, according to an exemplary embodiment.

FIG. 10 is a flow diagram illustrating the steps for determining individual fluid flow rates from a sensor receiving cumulative signals from multiple pulsatile signal transmitters, according to an exemplary embodiment. Using flow rates at pump A and pump B of cassette 56*a* as an example, the pressure sensor PS4 disposed along the flow path associated with pump B may receive cumulative pressure signals from both pumps A and B, as shown in step 90 of FIG. 10. The cumulative pressure signal used for determining individual fluid flow rates may be obtained over a specific duration. In one embodiment, the duration may be approximately 2-10 seconds. At step 91, a frequency analysis, e.g., a fast Fourier transform (FFT), may be conducted on the cumulative pressure signal obtained over the duration in step 90 to transform the cumulative signal from a time domain to a frequency domain, e.g., frequency amplitude spectrum. At step 92, two peaks may be identified from the frequency amplitude spectrum, wherein one of the peaks corresponds to pump A and the other corresponds to pump B. At step 93, Equation 3 may be used to convert the frequencies obtained in step 92 into pump flow rates. The flow rates obtained in step 93 may be identified and/or deduced as corresponding to pump A or pump B based on known parameters, such as proximity to commanded and/or expected flow rates. The flow rates obtained in step 93 may also be identified and/or deduced as corresponding to pump A or pump B based on knowledge regarding flow rates in relation to each other. For example, if pump A is expected to pump at a higher flow rate than pump B at a given time, the higher flow rate obtained in step 92 may be identified as corresponding to pump A, and the lower flow rate obtained in step 92 may be identified as corresponding to pump B. The controller may be programmed to continuously, periodically, and/or on a rolling basis repeat steps 90-93 in FIG. 10 to process pulsatile signal inputs to control the separation process.

Without limiting the foregoing description, in accordance with one aspect of the subject matter herein, there is provided a system for monitoring and controlling a fluid procedure. A reusable separation apparatus is controlled by a microprocessing controller. A pressure sensor is in communication with the controller. A sterile circuit is configured to associate with the reusable separation apparatus and provides a first fluid flow path in association with the pressure sensor and a first pump configured to transmit pulsatile pressure signals to the pressure sensor during operation in association with the first fluid flow path. The reusable apparatus and the controller are configured to 1) receive from the pressure sensor one or more pressure signals comprising the pulsatile pressure signals transmitted by the first pump, 2) perform a frequency analysis of the one or more pressure signals received by the pressure sensor over a time duration, 3) derive a first rotation rate of the first pump or a first fluid flow rate at the first pump from the frequency analysis, and 4) provide at least one response action based on the first rotation rate or the first fluid flow rate.

In accordance with a second aspect which may be used or combined with the immediately preceding aspect, a second fluid flow path is in association with a second pump of the reusable separation apparatus. A resilient element is in communication with the first fluid flow path and the second fluid flow path. The reusable apparatus and the controller are further configured to derive a second rotation rate of the second pump or a second fluid flow rate at the second pump from the frequency analysis, and provide at least one response action based on the second rotation rate or the second fluid flow rate.

In accordance with a third aspect which may be used or combined with any of the preceding aspects, the time duration is within a range of 2-10 seconds.

In accordance with a fourth aspect which may be used or combined with any of the preceding aspects, the frequency analysis comprises a fast Fourier transform.

In accordance with a fifth aspect which may be used or combined with any of the preceding aspects, the controller is configured to receive a rotation rate of the first pump or a fluid flow rate at the first pump during the time duration exclusively from the pressure sensor.

In accordance with a sixth aspect which may be used or combined with the second aspect, the resilient element comprises a porous membrane.

In accordance with a seventh aspect which may be used or combined with the second and sixth aspects, the resilient element comprises a material reactive to pressure changes originating from one or both of the first and second fluid flow paths.

In accordance with an eighth aspect which may be used or combined with the second, sixth aspects, and seventh aspects, the reusable apparatus and the controller are further configured to identify 1) the first rotation rate or the first fluid flow rate and 2) the second rotation rate or the second fluid flow rate flow rates as corresponding respectively to the first pump and the second pump based on commanded flow rates of the first and second pumps.

In accordance with a ninth aspect which may be used or combined with any of the preceding aspects, the controller is configured monitor and control the fluid procedure by repeating steps 1-4 continuously, periodically, and/or on a rolling basis.

In accordance with a tenth aspect, there is provided a computer-implemented method for monitoring fluid flow rates during a fluid procedure. A first pump is provided configured to transmit pulsatile signals during operation in association with a first fluid flow path. A sensor is provided in communication with the first fluid flow path and configured to receive the pulsatile signals from the first pump. A controller is provided in communication with the sensor and the first pump. The controller performs a frequency analysis on one or more signals received by the sensor over a time duration. A first rotation rate of the first pump or a first fluid flow rate at the first pump is calculated from the frequency analysis. At least one response action is provided based on the first rotation rate or the first fluid flow rate.

In accordance with an eleventh aspect which may be used or combined with the immediately preceding aspect, a second pump is provided configured to transmit pulsatile signals during operation in association with a second fluid flow path. The second pump is in communication with the controller. A resilient element is provided in communication with the first fluid flow path and the second fluid flow path. A second rotation rate of the second pump or a second fluid flow rate at the second pump is calculated from the frequency analysis. At least one response action is provided based on the second rotation rate or the first fluid flow rate.

In accordance with a twelfth aspect which may be used or combined with any of the tenth and eleventh aspects, the response action comprises altering the concentration of the retentate exiting the membrane separator by 0.1-5%.

In accordance with a thirteenth aspect which may be used or combined with any of the tenth through twelfth aspects, the frequency analysis comprises a fast Fourier transform.

In accordance with a fourteenth aspect which may be used or combined with any of the tenth through thirteenth aspects, the controller is configured to receive a rotation rate of the first pump or a fluid flow rate at the first pump during the time duration exclusively from the sensor.

In accordance with a fifteenth aspect which may be used or combined with any of the tenth through fourteenth aspects, the pulsatile signals comprise pulsatile pressure signals.

In accordance with a sixteenth aspect which may be used or combined with the eleventh aspect, the resilient element comprises a porous membrane.

In accordance with a seventeenth aspect which may be used or combined with the eleventh or sixteenth aspect, the resilient element comprises a material reactive to pressure changes originating from one or both of the first and second fluid flow paths.

In accordance with an eighteenth aspect which may be used or combined with any of the eleventh, sixteenth, or seventeenth aspects, 1) the first rotation rate or the first fluid flow rate and 2) the second rotation rate or the second fluid flow rate flow rates are identified as corresponding respectively to the first pump and the second pump based on commanded flow rates of the first and second pumps.

In accordance with a nineteenth aspect which may be used or combined with any of the eleventh and sixteenth through eighteenth aspects, steps 1-6 are repeated continuously, periodically, and/or on a rolling basis.

In accordance with a twentieth aspect, there is provided a system for monitoring and controlling a fluid procedure. A reusable separation apparatus is controlled by a microprocessing controller. A pressure sensor is in communication with the controller. A sterile circuit is configured to associate with the reusable separation apparatus and provide a first fluid flow path in association with a first pump and the pressure sensor and a second fluid flow path in association with a second pump. The first pump is configured to transmit pulsatile pressure signals to the pressure sensor during operation in association with the first fluid flow path and the second pump is also configured to transmit pulsatile pressure signals to the pressure sensor during operation in association with the second fluid flow path. A resilient element is in communication with the first and second fluid flow paths. The resilient element comprises a material reactive to pressure changes originating from one or both of the first and second fluid flow paths. The reusable apparatus and the controller are configured to receive from the pressure sensor one or more pressure signals comprising pulsatile pressure signals from the first and second pumps, perform a fast Fourier transform of the one or more pressure signals received by the pressure sensor over a time duration, derive a first rotation rate of the first pump or a first fluid flow rate at the first pump from the frequency analysis, derive a second rotation rate of the second pump or a second fluid flow rate at the second pump from the frequency analysis, and provide at least one response action based on a) the first rotation rate or the first fluid flow rate and b) the second rotation rate or the second fluid flow rate.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:
1. A system for monitoring and controlling a fluid procedure, the system comprising:
   a reusable separation apparatus controlled by a microprocessing controller, wherein the reusable separation apparatus comprises a first pump, a second pump, and a pressure sensor in communication with the controller;
   a sterile circuit configured to associate with the reusable separation apparatus and provide a first fluid flow path in association with the pressure sensor and the first pump configured to transmit pulsatile pressure signals to the pressure sensor during operation in association with the first fluid flow path and a second fluid flow path in association with the pressure sensor and the second pump configured to transmit pulsative pressure signals to the pressure sensor during operation in association with the second fluid flow path;

wherein the reusable apparatus and the controller are configured to:
1) receive from the pressure sensor one or more pressure signals comprising the pulsatile pressure signals transmitted by the first pump and the second pump;
2) perform a frequency analysis of the one or more pressure signals received by the pressure sensor over a time duration;
3) derive a first rotation rate of the first pump or a first fluid flow rate at the first pump from the frequency analysis;
4) derive a second rotation rate of the second pump or a second fluid flow rate at the second pump from the frequency analysis; and
5) provide at least one response action based on a) the first rotation rate or the first fluid flow rate and/or b) the second rotation rate or the second fluid flow rate, the at least one response action altering at least one aspect of the fluid procedure and/or generating an alert, wherein each of the first rotation rate or the first fluid flow rate and the second rotation rate or the second fluid flow rate is determined based on said one or more pressure signals from only the pressure sensor and not also based on pressure signals from a second pressure sensor.

2. The system of claim 1, further comprising:
a resilient element in communication with the first fluid flow path and the second fluid flow path.

3. The system of claim 2, wherein the resilient element comprises a porous membrane.

4. The system of claim 2, wherein the resilient element comprises a material reactive to pressure changes originating from one or both of the first and second fluid flow paths.

5. The system of claim 1, wherein the time duration is within a range of 2-10 seconds.

6. The system of claim 1, wherein the frequency analysis comprises a fast Fourier transform.

7. The system of claim 1, wherein the controller is configured to receive a rotation rate of the first pump or a fluid flow rate at the first pump during the time duration exclusively from the pressure sensor.

8. The system of claim 1, wherein the reusable apparatus and the controller are further configured to identify 1) the first rotation rate or the first fluid flow rate and 2) the second rotation rate or the second fluid flow rate flow rates as corresponding respectively to the first pump and the second pump based on commanded flow rates of the first and second pumps.

9. The system of claim 1, wherein the controller is configured monitor and control the fluid procedure by repeating steps 1-5 continuously, periodically, and/or on a rolling basis.

10. The system of claim 1, wherein the at least one aspect of the fluid procedure comprises a fluid flow rate.

11. The system of claim 1, wherein the at least one aspect of the fluid procedure comprises a pump rate.

12. The system of claim 1, wherein the at least one aspect of the fluid procedure comprises a separation rate.

13. The system of claim 1, wherein the at least one aspect of the fluid procedure comprises a spin rate.

14. The system of claim 1, wherein the at least one aspect of the fluid procedure comprises a target parameter.

15. The system of claim 1, wherein the at least one response action includes suspending the fluid procedure.

16. A computer-implemented method for monitoring fluid flow rates during a fluid procedure, comprising:

1) providing a first pump configured to transmit pulsatile signals during operation in association with a first fluid flow path and a second pump configured to transmit pulsatile signals during operation in association with a second fluid flow path;
2) providing a sensor in communication with the first and second fluid flow paths and configured to receive the pulsatile signals from the first pump and the second pump;
3) providing a controller in communication with the sensor, the first pump, and the second pump;
4) performing via the controller a frequency analysis on one or more signals received by the sensor over a time duration;
5) calculating a first rotation rate of the first pump or a first fluid flow rate at the first pump from the frequency analysis;
6) calculating a second rotation rate of the second pump or a second fluid flow rate at the second pump from the frequency analysis; and
7) providing at least one response action based on a) the first rotation rate or the first fluid flow rate and/or b) the second rotation rate or the second fluid flow rate, the at least one response action altering at least one aspect of the fluid procedure and/or generating an alert, wherein each of the first rotation rate or the first fluid flow rate and the second rotation rate or the second fluid flow rate is determined based on said one or more signals received by only the sensor and not also based on signals received by a second sensor.

17. The computer-implemented method of claim 16, further comprising:
providing a resilient element in communication with the first fluid flow path and the second fluid flow path.

18. The computer-implemented method of claim 17, wherein the resilient element comprises a porous membrane.

19. The computer-implemented method of claim 17, wherein the resilient element comprises a material reactive to pressure changes originating from one or both of the first and second fluid flow paths.

20. The computer-implemented method of claim 16, wherein the time duration is within a range of 2-10 seconds.

21. The computer-implemented method of claim 16, wherein the frequency analysis comprises a fast Fourier transform.

22. The computer-implemented method of claim 16, wherein the controller is configured to receive a rotation rate of the first pump or a fluid flow rate at the first pump during the time duration exclusively from the sensor.

23. The computer-implemented method of claim 16, wherein the pulsatile signals comprise pulsatile pressure signals.

24. The computer-implemented method of claim 16, further comprising identifying 1) the first rotation rate or the first fluid flow rate and 2) the second rotation rate or the second fluid flow rate flow rates as corresponding respectively to the first pump and the second pump based on commanded flow rates of the first and second pumps.

25. The computer-implemented method of claim 16, further comprising repeating steps 1-7 continuously, periodically, and/or on a rolling basis.

26. A system for monitoring and controlling a fluid procedure, the system comprising:
a reusable separation apparatus controlled by a microprocessing controller, wherein the reusable separation apparatus comprises a pressure sensor in communication with the controller;

a sterile circuit configured to associate with the reusable separation apparatus and provide a first fluid flow path in association with a first pump and the pressure sensor and a second fluid flow path in association with a second pump;

wherein the first pump is configured to transmit pulsatile pressure signals to the pressure sensor during operation in association with the first fluid flow path and the second pump is also configured to transmit pulsatile pressure signals to the pressure sensor during operation in association with the second fluid flow path;

a resilient element in communication with the first and second fluid flow paths, wherein the resilient element comprises a material reactive to pressure changes originating from one or both of the first and second fluid flow paths;

wherein the reusable apparatus and the controller are configured to:

1) receive from the pressure sensor one or more pressure signals comprising pulsatile pressure signals from the first and second pumps;

2) perform a fast Fourier transform of the one or more pressure signals received by the pressure sensor over a time duration;

3) derive a first rotation rate of the first pump or a first fluid flow rate at the first pump from the frequency analysis;

4) derive a second rotation rate of the second pump or a second fluid flow rate at the second pump from the frequency analysis; and 5) provide at least one response action based on a) the first rotation rate or the first fluid flow rate, and b) the second rotation rate or the second fluid flow rate, the at least one response action altering at least one aspect of the fluid procedure and/or generating an alert, wherein each of the first rotation rate or the first fluid flow rate and the second rotation rate or the second fluid flow rate is determined based on said one or more pressure signals from the pressure sensor and not also based on pressure signals from a second pressure sensor.

* * * * *